United States Patent [19]

Kobayashi

[11] Patent Number: 4,469,481
[45] Date of Patent: Sep. 4, 1984

[54] APPARATUS FOR INFUSING MEDICATION

[75] Inventor: Susumu Kobayashi, Fujinomiya, Japan

[73] Assignee: Terumo Corporation, Tokyo, Japan

[21] Appl. No.: 388,918

[22] Filed: Jun. 16, 1982

[30] Foreign Application Priority Data

Jun. 23, 1981 [JP] Japan .................................. 56-96043

[51] Int. Cl.³ .......................................... A61M 37/00
[52] U.S. Cl. ...................................... 604/67; 604/131;
604/151; 128/DIG. 1; 128/DIG. 12
[58] Field of Search .................... 604/67, 65, 131, 151;
128/DIG. 13, DIG. 1, DIG. 12

[56] References Cited

U.S. PATENT DOCUMENTS

| 4,111,198 | 9/1978 | Marx et al. | 128/DIG. 13 |
| 4,282,872 | 8/1981 | Franetzki et al. | 604/67 |
| 4,299,218 | 11/1981 | Knigge et al. | 604/67 |
| 4,328,801 | 5/1982 | Marx et al. | 604/67 |
| 4,391,598 | 7/1983 | Thompson | 128/DIG. 13 |

FOREIGN PATENT DOCUMENTS

| 2775 | 7/1979 | European Pat. Off. | |
| 2451424 | 5/1976 | Fed. Rep. of Germany. | |
| 2009453 | 6/1979 | United Kingdom. | |
| 2011652A | 7/1979 | United Kingdom | 604/67 |
| 2039083 | 7/1980 | United Kingdom. | |

Primary Examiner—Lee S. Cohen
Assistant Examiner—Steven Falk
Attorney, Agent, or Firm—Frishauf, Holtz, Goodman & Woodward

[57] ABSTRACT

An apparatus for infusing liquid medication such as insulin into a living body has a memory for storing a basic pattern and meal patterns which decide the medication infusion dose in accordance with time. The basic pattern is designated under ordinary conditions, with a meal pattern being designated for a predetermined period of time when desired. With the passage of the predetermined period, the basic pattern is restored, the address of the basic pattern being designated according to the actual time. When a pattern is selected, the one actually addressed and read out of the memory is that appropriate for the time of day. The pattern information read out of the memory is applied to means for infusing the liquid medication into the living body, the dose of the medication conforming to the specific pattern.

14 Claims, 19 Drawing Figures

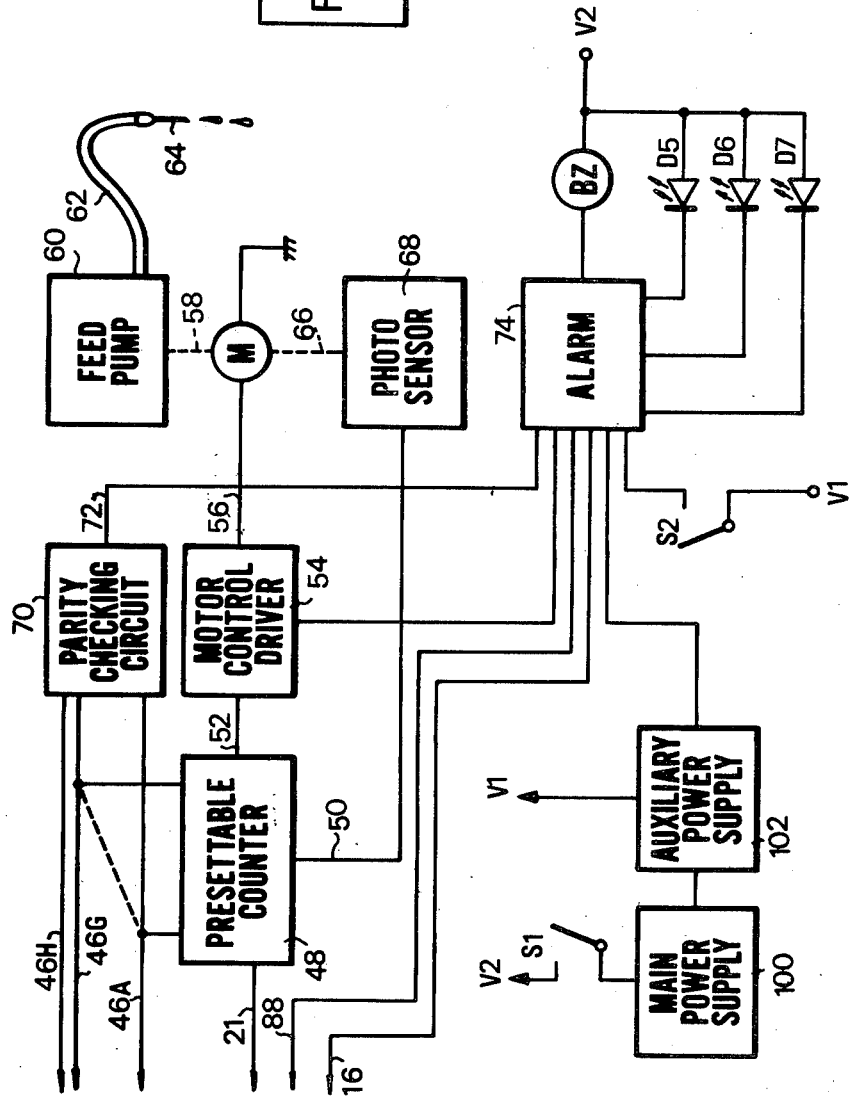

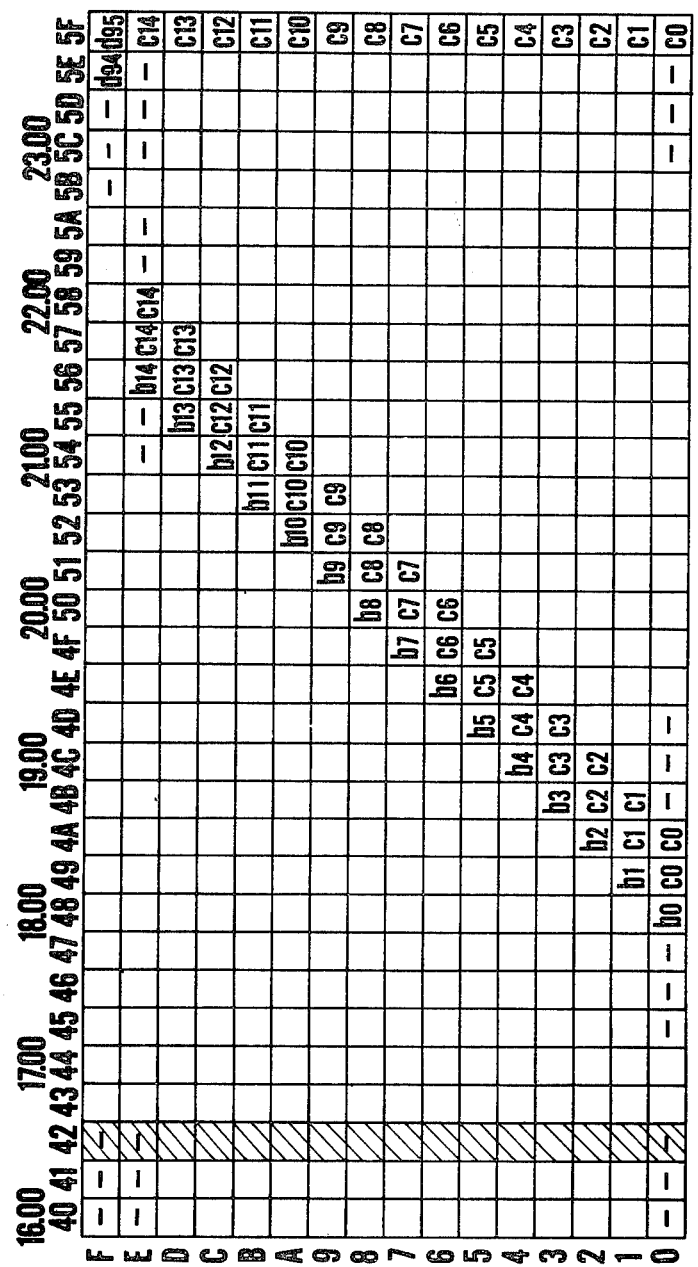

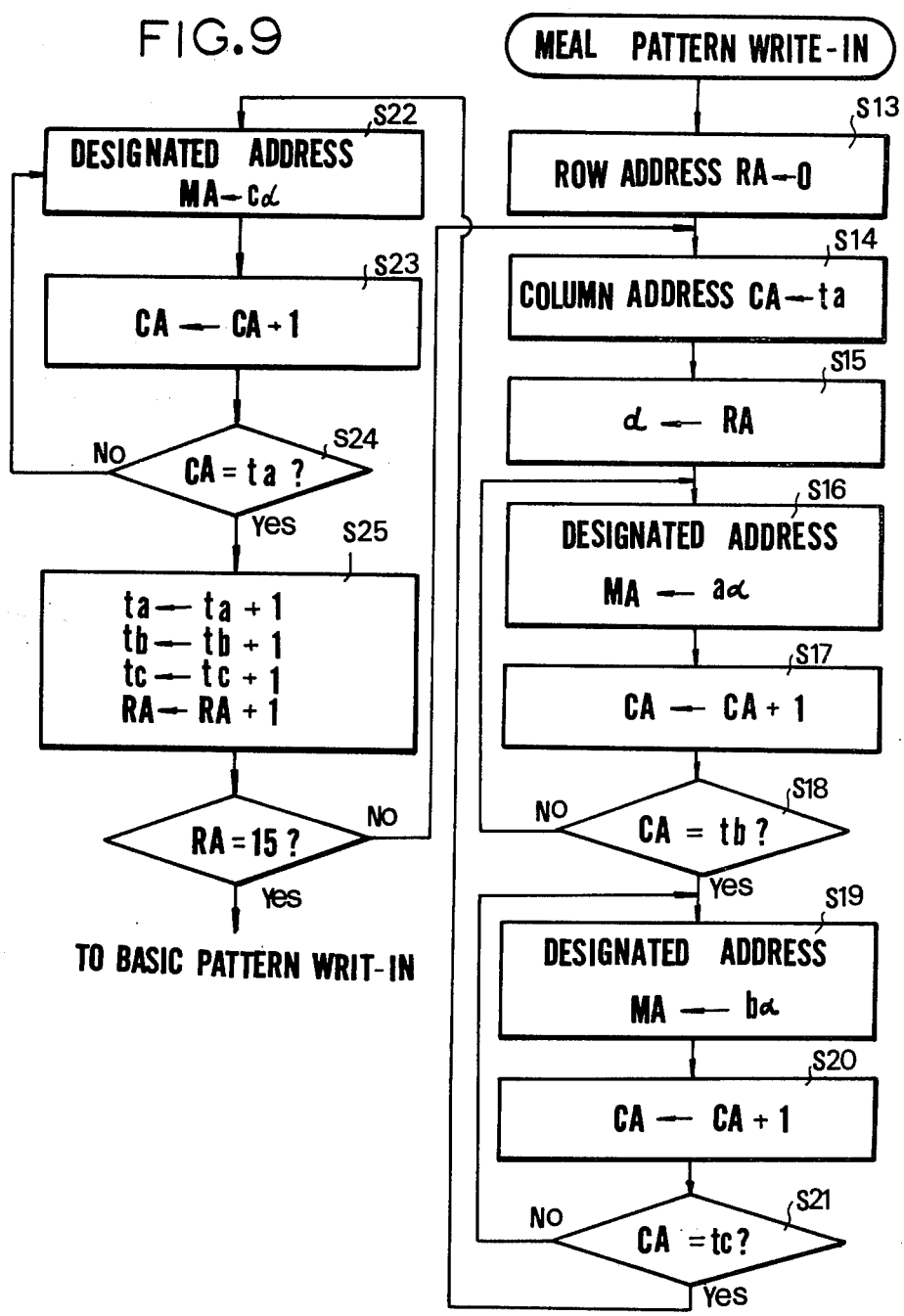

APPARATUS FOR INFUSING MEDICATION

BACKGROUND OF THE INVENTION

1. Field of the Invention

This invention relates to an apparatus for infusing liquid medication and, more particularly, to a liquid medication infusing apparatus which includes liquid feeding means for infusing liquid medication into a living body, the quantity of liquid medication infused conforming to a control signal, means for generating time information, and a control circuit connected to the time information generating means for producing control signals.

2. Description of the Prior Art

There have been numerous disclosures concerning the medication infusing apparatus of the above-described type, particularly for the infusion of insulin in the treatment of diabetics. One example of such a previously disclosed apparatus infuses the insulin on the basis of pre-programmed quantities. In other words, a schedule of the patient's daily activities is standardized or set beforehand, and a program is prepared according to which the insulin dose is increased or decreased with time in accordance with the set schedule. For instance, since there is a rise in the blood sugar level during meals, the insulin dose is programmed to increase three times per day during each mealtime. However, many diabetics lead active social lives and do not always take their meals at the designated hour. Accordingly, the infusion of the programmed insulin dose at the programmed time can result in an overdose and expose the patient to the danger of an abnormally low blood sugar level.

One proposed solution to the above problem is a system which constantly infuses a fixed, minimum required dose of the insulin and which comes equipped with a button that the patient depresses when he wishes to consume a meal. Depressing the button starts a pre-determined sequence in accordance with which the insulin dose is changed to supplement the fixed dose. With this system, however, the quantity of insulin infused under ordinary conditions is constant throughout the day irrespective of the time. The patient's activity, on the other hand, generally changes from one occasion to the next. Thus, even if the problem of insulin dose during meals is solved, the constant or basic insulin dose at other times should be different to conform to the rhythm of the patient's daily activities. For example, the required insulin dose during the daytime when the patient is active differs from the dose required at night when the patient is at rest or asleep. Another important factor is that the pattern of insulin infusion generally differs according to the length of each meal. In other words, the sequence through which the infused insulin dose varies is not the same for the breakfast, lunch and supper meals. Since a patient may miss or skip a meal for some reason or take a meal at other than the designated hour, there is a need for means which can take such occasions into account and infuse the insulin dose best suited for the patient's physiological needs at that time. Another requirement for such means is that it be capable of immediately restoring the ordinary insulin dose, or basic pattern, if the patient should operate the device incorrectly or at the wrong time or if, after having initiated the infusion of an insulin dose required for the duration of a meal, the patient should interrupt or be forced to miss that meal for some reason.

SUMMARY OF THE INVENTION

The present invention has been devised to eliminate the foregoing shortcomings encountered in the prior art, and has as its object to provide a medication infusing apparatus which is capable of infusing a liquid medication in doses which conform to the physiological conditions of the living body.

Another object of the present invention is to provide a medication infusing apparatus which is highly reliable and which responds quickly and accurately to changes in the physiological conditions of a living body.

A more specific object of the present invention is to provide a medication infusing apparatus in which infusion patterns for infusing medication in doses commensurate with a change in patient activity, are stored in memory at addresses that conform to time and to the infusion patterns, whereby the start of an infusion data read operation and the changeover from one infusion pattern to another are always controlled in relation to time.

Another object of the present invention is to provide a medication infusing apparatus which, by enabling a second infusion pattern to be selected and cancelled at will, assures a high degree of safety and places no restriction upon the daily activity of the patient using the apparatus.

Still another object of the present invention is to provide a medication infusing apparatus in which counter values that vary from a preset value to a specified value are allocated to first and second infusion patterns as address data, thereby facilitating control in relation to time.

Yet another object of the present invention is to provide a medication infusing apparatus in which infusion patterns can be rewritten by means of an externally located writing device, thereby enabling the effective utilization of the available memory and facilitating the correction and modification of the infusion patterns.

According to the present invention, the foregoing objects are attained by providing an apparatus for infusing liquid medication comprising time base means for generating time information, memory means for storing first and second infusion information for deciding a liquid medication infusion dose in accordance with time, a control circuit controlled by the time information generating means and including a first memory control circuit for selecting the first infusion information under ordinary conditions, selecting the second infusion information for a predetermined period of time in response to a selection operation, and for restoring the first infusion information upon the lapse of the predetermined time period, and a second memory control circuit, responsive to the time information, for reading out of the memory means an infusion dose dependent upon the time information and decided by the infusion information selected by the first memory control circuit, and infusion means driven in accordance with the infusion dose read out of the memory means for infusing the liquid medication into a living body.

According to one embodiment of the invention, the memory means includes a plurality of storage locations at the points of intersection between a set of row addresses and a set of column addresses, one set being decided in accordance with the time information, the other set being allocated in accordance with the first and second infusion information. The liquid medication which the infusion means infuses into the living body includes insulin. The first infusion information is a basic pattern, and the second infusion information is a meal pattern which includes at least a breakfast pattern, a lunch pattern or a supper pattern. In addition, the infusion means includes a motor driven at a substantially constant speed by a control signal for infusing the liquid medication into the living body. The second memory control circuit is adapted to read infusion doses out of the memory means at fixed time intervals. The control signal is generated by control signal generating means for a period of time corresponding to the dose read out of the memory means by the second memory control circuit.

More specifically, the foregoing objects are attained by an apparatus for infusing liquid medication, comprising time base means for generating time information, memory means for storing first and second infusion information for deciding a liquid medication infusion dose in accordance with time, the first and second infusion information being addressable through row and column address sets of which one set corresponds to the time information, first addressing means for designating, in accordance with the time information, the addresses in the set corresponding to the time information, second addressing means for designating addresses in the other address set in accordance with which of the first and second infusion information is selected, a first specific address being designated while the first infusion information prevails, a second specific address being designated when the second infusion information is selected, the second specific address being updated in accordance with time until the designated address returns to the first specific address of the first infusion information, and infusion means driven in accordance with infusion information read out of the memory means for infusing the liquid medication into the living body.

According to a preferred embodiment of the invention, the first addressing means and second addressing means include first and second counters, respectively, for counting clock pulses from the time generating means following division by a plurality of frequency divider stages. The apparatus further includes a discrimination circuit for discriminating a first specific counted value in the second counter to produce an inhibit signal which inhibits the second counter from counting the clock pulses, whereby the second counter preserves the specific count as an address of the first infusion data. Also provided are reset means for resetting the second counter which preserves the first specific counted value, whereby the second counter is preset to a specific value which corresponds to an address of the second infusion information. The counted value in the second counter, which varies from the preset specific value to the first specific value, is continuously allocated to the addresses that designate the first and second infusion information. The reset means comprises a switch, operative from outside the apparatus, for selecting the second infusion apparatus. Further, the discrimination circuit is adapted to discriminate a second specific counted value in the second counter for driving alarm signal means when the second specific counted value is discriminated, whereby the alarm means informs the patient of the fact that a predetermined time period has elapsed since the selection of the second infusion information.

The apparatus also includes selection means for selectively supplying the second counter of the second addressing means with the frequency-divided clock pulses, and with second clock pulses n-times higher in frequency concurrently provided by an earlier stage of the plurality of frequency divider stages. The selection means comprises a switch for interrupting the read-out of the second infusion information.

In still greater detail, the apparatus of the present invention comprises time base means for generating time information, readable/writable memory means for storing first and second infusion information for deciding a liquid medication infusion dose in accordance with time, the first and second infusion information being addressable through row and column address sets of which one set corresponds to the time information, first addressing means for designating, in accordance with time information, the addresses in the set corresponding to the time information, selection means connected to the output side of the first addressing means for selectively receiving address designating signals from the first addressing means as well an externally applied address designating signal, second addressing means for designating addresses in the other address set in accordance with which of the first and second infusion information is selected, a first specific address being designated while the first infusion information prevails, a second specific address being designated when the second infusion information is selected, the second specific address being updated in accordance with time until the designated address returns to the first specific address of the first infusion information, selection means connected to the output side of the second addressing means for selectively receiving address designating signals from the second addressing means as well as externally applied address designating signals, data input means for receiving externally written data, means for controlling the writing and reading of data to and from the memory means, write signal input means for applying a write control signal to the write/read control means when data is externally written, means for generating an internal clock applied to the write/read control means, high-impedance setting means connected to the output side of the internal clock generating means for selectively receiving the internal clock as well as an externally applied clock, and infusion means driven in accordance with infusion information read out of the memory means for infusing the liquid medication into a living body. Provided on the outer side of the apparatus are input terminals for receiving externally applied address inputs, data inputs, a write control signal and a clock input.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 1B and 1C are block diagrams illustrating an embodiment of a programmable medication infusing apparatus according to the present invention;

FIG. 1A shows how the circuits in FIGS. 1B and 1C are interconnected;

FIGS. 2A and 2B show a memory map of basic pattern and meal pattern data;

FIG. 9 is a flowchart showing steps for writing in meal pattern data;

DESCRIPTION OF THE PREFERRED EMBODIMENT

Figure 1B:
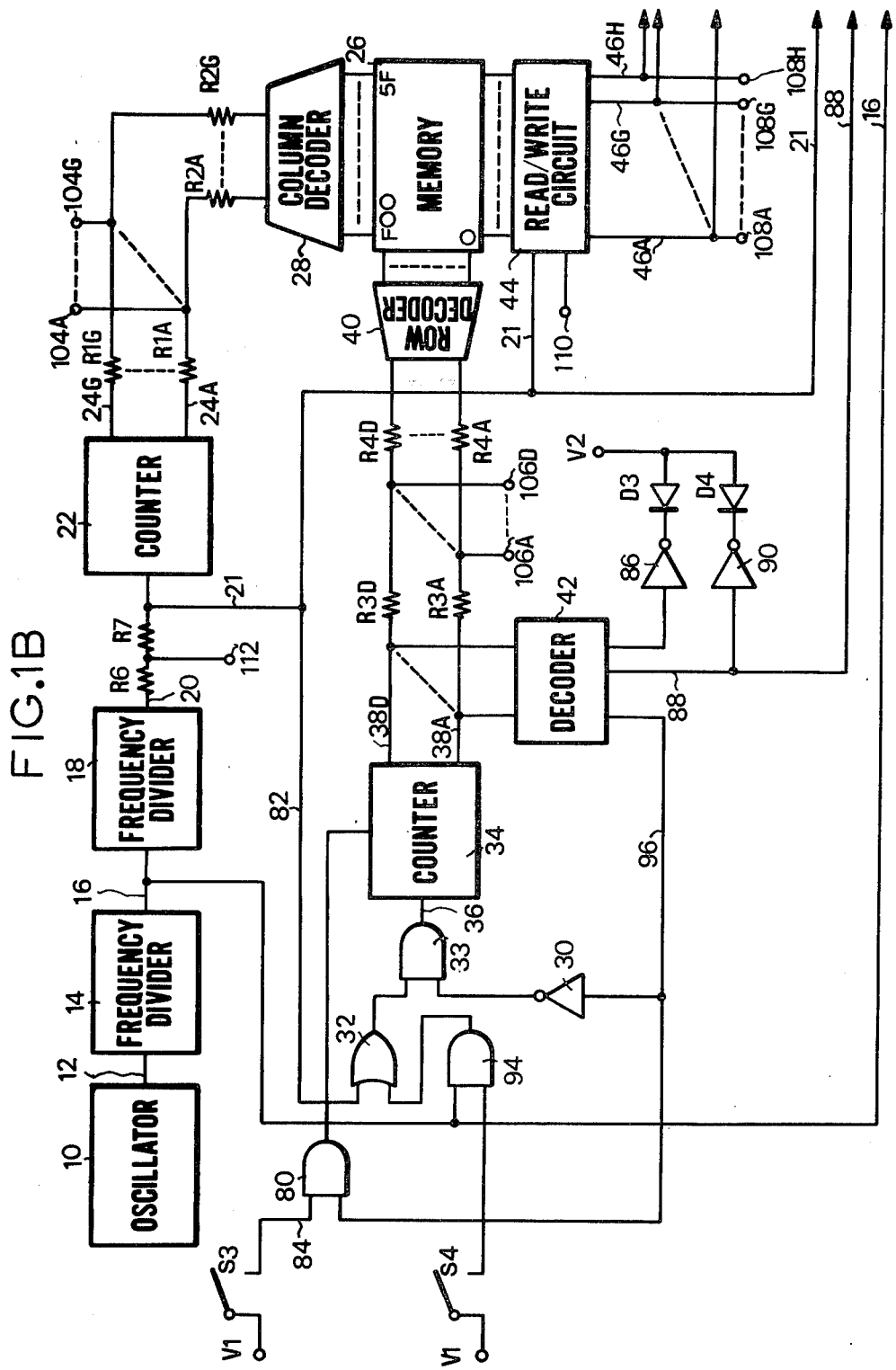

FIGS. 1B and 1C are functional block diagrams illustrating an embodiment of a liquid medication infusing apparatus according to the present invention. The circuitry shown in FIG. 1B is connected with that shown in FIG. 1C through leads 46A through 46H as well as leads 21, 88, and 16. This is shown in FIG. 1A. The apparatus includes an oscillator 10 which may advantageously employ a tuning fork quartz vibrator, not shown, and generate a reference frequency of, say, 32,768 Hertz. The high-frequency output 12 of the oscillator 10 is connected to the input side of a first frequency divider 14 which may comprise a 14-stage binary counter for dividing the high-frequency signal down to frequencies of 2048 Hertz, 4 Hertz and 2 Hertz. To simplify the illustration, these three low-frequency signals are shown as being delivered on line 16; in actuality, each signal is delivered over a separate line. The two-Hertz signal on line 16 is applied to a second frequency divider circuit 18 where it is divided by 120 to produce a one-minute clock signal on line 20. For this purpose the frequency divider 18 may comprise a 12-stage binary counter. The one-minute clock signal from the frequency divider 18 is connected to a first counter 22 through resistors R6, R7. The counter 22 comprises a circulating counter circuit whose status returns to zero upon counting 1440 of the one-minute clock signals, or pulses. In other words, the counter 22 is capable of counting up to 1440 of the one-minute clock pulses, so that its content returns to zero after a period of 24 hours. Counter 22 has seven output lines 24A through 24G which are connected to the input side of a column decoder 28 for a memory 26 through respective resistors R1A through R1G and R2A through R2G. The signals on output lines 24A through 24G represent a parallel array of bits which specify a seven-digit binary number. The least significant bit, which appears on line 24A, is incremented when counter 22 counts 15 of the one-minute clock pulses. Accordingly, the parallel bits on lines 24A through 24G are incremented one at a time every 15 minutes and return to zero when 24 hours elapse.

The column decoder 28 develops the seven-digit binary number (whose maximum value is 96) input on lines 24A through 24G into 96 output signals in order to selectively designate column addresses OO through 5F of locations in memory 26.

The one-minute clock pulse from frequency divider 18 is connected also to the input side of a second counter 34 through line 21, OR gate 32, AND gate 33 and line 36. Counter 34 produces four output signals on lines 38A through 38D that are connected to the input side of a row decoder 40 for the memory 26 through respective resistors R3A through R3D and R4A through R4D. Counter 34 is a resettable counter which is capable of counting a maximum of 225 of the one-minute clock pulses (equivalent to 3 hours and 45 minutes) arriving on line 36. The four signals on lines 38A through 38D, which correspond to the four high-order bits of eight bits, represent a parallel array of bits that specify a four-digit binary number. The least significant bit, which appears on line 38A, is incremented every 15 minutes, so that when counter 34 counts up to its capacity, all four of the bits on lines 38A through 38D will express a significant condition, namely the hexadecimal number "F". The row decoder 40 for memory 26 develops the four-digit binary number input on lines 38A through 38D into 16 output signals for selectively designating row addresses O through F of locations in memory 26.

The output signals from counter 34 on lines 38A throug 38D are connected also to a decoder 42 which is adapted to sense a specific value represented by these four signals, which value may be the fullcount of counter 34 (all "1"s), by way of example. This will be described below in further detail.

An inverter 30 is connected to the clock input terminal of counter 34 through AND gate 33. When the decoder 42 senses a full count in counter 34, the signal delivered by the decoder on line 96 goes high and is inverted by the inverter 30. When line 96 is high, therefore, counter 34 is prohibited from counting the clock input and retains the full count.

Figure 2A:
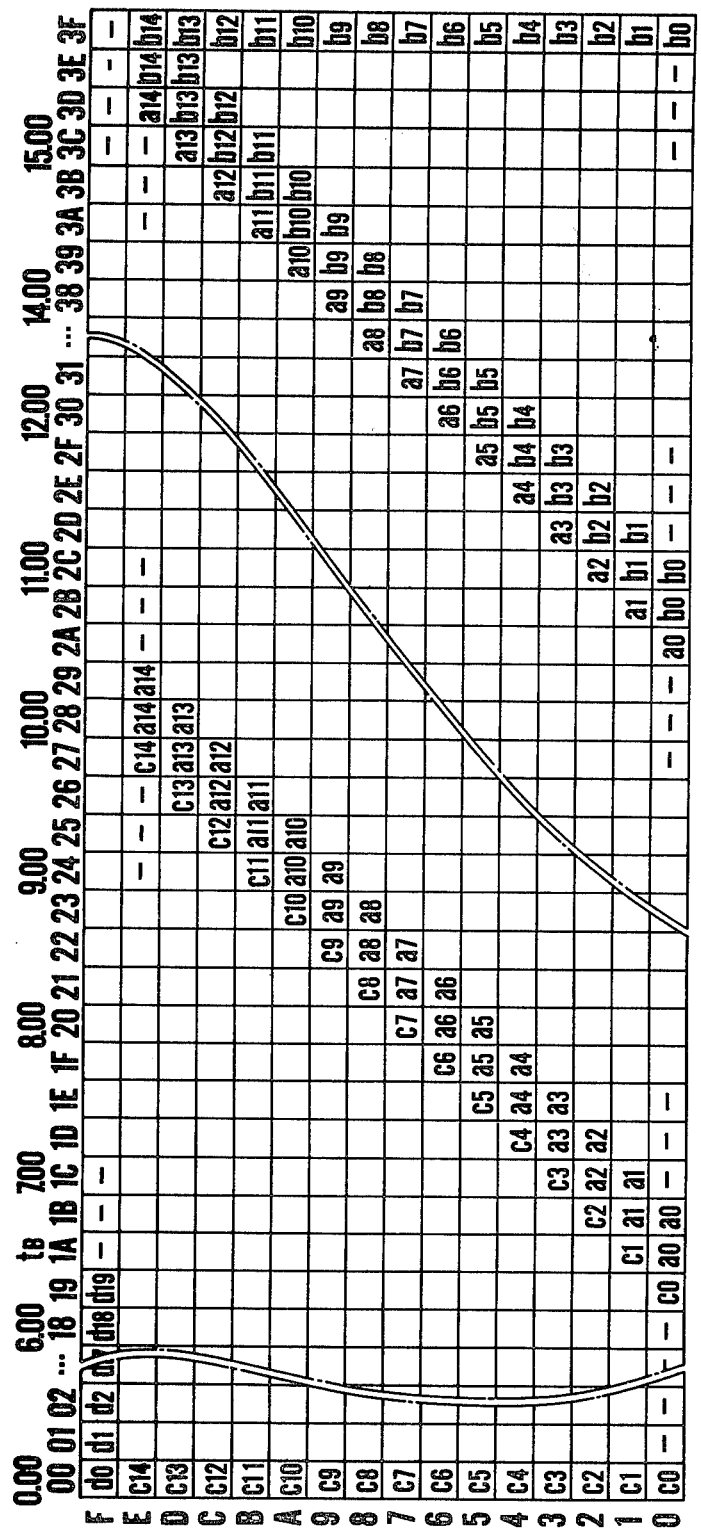

The memory 26 is a 16K-bit complimentary metal oxide semiconductor (CMOS) static random access memory (RAM). FIGS. 2A and 2B, which are useful in describing a memory map stored in the memory 26, illustrates column addresses OO through 5F horizontally and row addresses O through F vertically. As mentioned above, the column addresses OO through 5F are incremented one by one every 15 minutes by the counter 22, so that the addresses are updated column-by-column every 15 minutes over a period of 24 hours from 00:00 to 24:00, in terms of a 24-hour clock. When the last address 5F is reached, therefore, the cycle repeats starting with the address OO after the elapse of 15 minutes. For the sake of reference the memory map of FIGS. 2A and 2B includes the hourly times corresponding to every fourth column address, starting with address OO (00:00). The row addresses O through F also are incremented every 15 minutes, by the counter 34, so that address F is reached 3 hours and 45 minutes after address O is designated.

Each point of intersection of a row address and column address stores eight bits of data inclusive of a single parity bit. The eight-bit data corresponds to the dose of a liquid medication, such as insulin, to be infused into a living body. More specifically, according to this embodiment of the invention, each point of intersection stores 1/15 of the insulin dose to be infused into the living body in 15 minutes. A more detailed discussion of this point will be described hereinbelow.

A read/write circuit 44 is connected to memory 26, as shown in FIG. 1B. The read/write circuit 44 includes a memory register (not shown) for executing a read or write operation with respect to the designated row and column addresses of memory 26, and has eight outputs 46A through 46H. The output signals delivered on lines 46A through 46G are connected to the input side of a presettable counter 48, shown in FIG. 1C. Presettable counter 48 is a so-called downcounter which, in response to pulses arriving at its input 50, successively counts down a preset value to zero, the preset value being established by the signals which arrive on lines 46A through 46G. The output of counter 48, which appears on line 52, is connected to a motor control driver circuit 54 whose output 56 is in turn connected to a motor M. The motor M is mechanically coupled to a liquid feeding pump 60, as indicated by the dashed line 58 in FIG. 1C, and is adapted to drive the pump in order to dispense liquid medication such as insulin into a living body through a feed tube 62 and catheter 64.

Further, motor M is optically coupled to a photosensor 68 as indicated by the dashed line 66 in FIG. 1C. By way of example, the photosensor 68 may comprise a light-emitting diode (not shown) and a phototransistor (not shown) which receives the light emitted by the light-emitting diode. A shielding plate is mounted on the rotary shaft (not shown) of the motor M and, rotating in unison with the motor, is adapted to intermittently block the beam of light from the light-emitting diode. Thus the photosensor 68 generates pulses on its output line 50 as the motor M rotates. These pulses are applied to the presettable counter 48 and decrement the content of the counter, as mentioned above.

The eight output signals on lines 46A through 46H from the read/write circuit 44 are applied also to a parity check circuit 70 whose output 72 is connected to an alarm circuit 74.

The one-minute clock pulse from frequency divider 18 is coupled to the presettable counter 48 over line 21. When the clock pulse arrives, the presettable counter 48 receives, as an initial value, the seven-bit data on lines 46A through 46G read out of the designated addresses of memory 26 by the read/write circuit 44. When counter 48 is thus preset to an initial value, its output on line 52 goes high (logic "1"), in response to which the motor control driver circuit 54 drives the motor M. The motor M, which rotates at a constant speed of 2000 to 3000 rpm, is coupled to the feeding pump 60 through a reduction mechanism (not shown) to infuse the liquid medication in small amounts. As the motor M rotates, the phototransistor of photosensor 68 generates a single pulse each time the light shielding plate interrupts the beam of light from the light-emitting diode. As stated earlier, these pulses enter the presettable counter 48 which responds by counting down the preset value as each pulse arrives. The counter output delivered to the motor control driver circuit 54 remains high until the content of the counter is stepped down to zero. When this occurs, the counter output on line 52 goes low (logic "0"), whereby the motor control driver circuit 54 applies a braking action to the motor M to stop the motor instantaneously. This halts the infusion of insulin via the feed pump 60.

The data stored in the memory map (FIGS. 2A and 2B) of memory 26 has the following organization. As mentioned above, eight-bit data which includes a parity bit is stored at the cross points of the row and column addresses. This data is related to the insulin dose infused into the living body by each single revolution of the motor M. As described above, the motor M is driven whenever the presettable counter 48 is set to an initial value read out of the memory 26, the presetting of the counter 48 taking place in response to the one-minute clock pulse which arrives on line 21. Consequently, motor M is driven into rotation each time the one-minute clock pulse is produced by the frequency divider 18, that is, at a rate of once per minute. It may be recalled that the column addresses 00 through 5F of memory 26 are incremented one by one each time the first counter 22 counts 15 of the one-minute clock pulses that arrive on line 21. Counter 22 therefore designates one column address for 15 minutes before moving on to the next column address. Accordingly, each cross point of a row address and column address on the memory map stores a value corresponding to a dose which is 1/15 of the insulin dose to be infused in 15 minutes. This value is the initial value to be preset in presettable counter 48 and thus corresponds to the time period during which the fractional dose of insulin can be infused into the living body by the feed pump 60 as the motor M is driven.

Figure 3A:
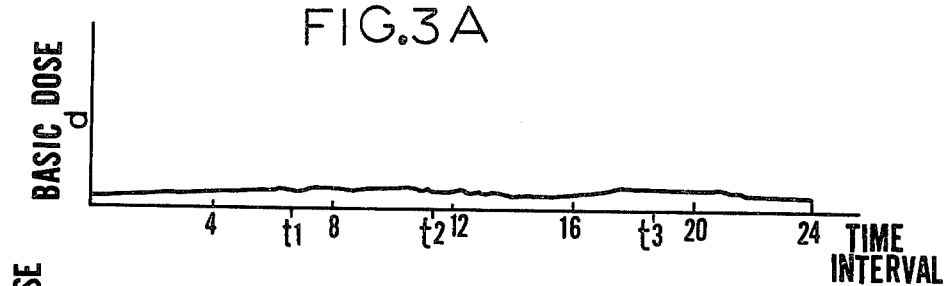
FIGS. 3A through 3E are graphs showing examples of insulin infusion patterns according to the present invention.

Data d0, d1, ..., d95 is written into the row address F of the memory map, as shown in FIGS. 2A and 2B. These items of data specify the minimum insulin infusion dose required by a diabetic when the apparatus of the invention is adapted for such treatment. Each data item d0, d1, ..., d95 may serve as an initial value preset in presettable counter 48 and corresponds to a value which is 1/15 of the minimum insulin dose required for infusion during each 15-minute period of one day, obtained by dividing 24 hours into 15-minute units. These values make up what is referred to as a basic pattern, one example of which is shown in FIG. 3A. The basic pattern is decided by the physician and is based on a variety of factors such as the patient's condition, age, sex and activity. According to the present invention, therefore, the basic pattern is divided into 15-minute units, and the units can be written into the locations specified by the column addresses 00 through 5F at the row address F.

Figure 3B:
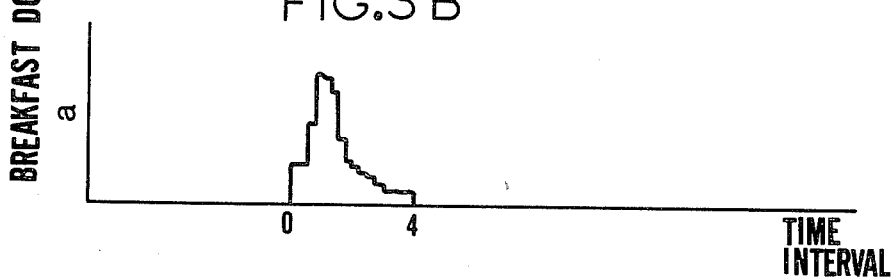
Figure 3C:
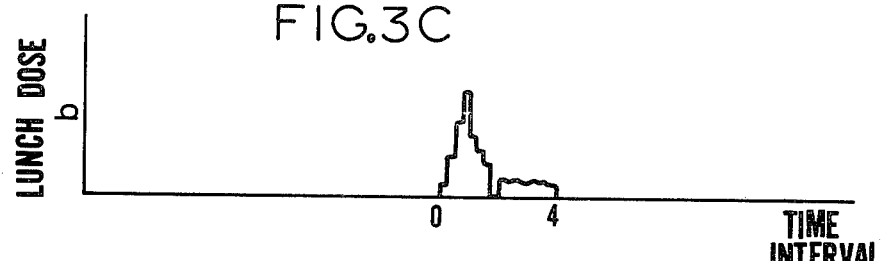
Figure 3D:
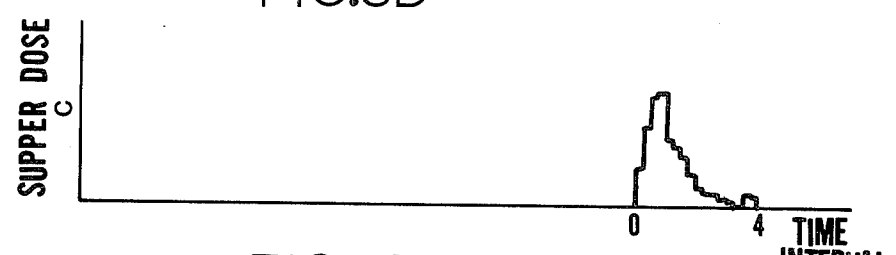

Since there is a rise in the blood sugar level when a meal is consumed, a diabetic must be administered an insulin dose which is greater than normal in order to prevent an excessively high blood sugar level. To this end, the apparatus of the present invention makes it possible to determine an insulin dose, which is greater than the normal dose, for infusion over a period of time which brackets mealtime. This is referred to as a meal pattern, examples of which are shown in FIGS. 3B, 3C and 3D, representing a breakfast pattern a, lunch pattern b, and supper pattern c, respectively. The insulin doses that make up these meal patterns also can be determined in terms of 15-minute units, as will be understood from FIGS. 3B, 3C and 3D, independently of the basic pattern d. Moreover, the meal patterns can be determined independently of one another.

The meal pattern data is written into the locations specified by row addresses 0 through E of the memory map shown in FIGS. 2A and 2B. For example, infusion dose data a0 for the breakfast meal is written into row address 0 at column address 1A, infusion dose data a1 for the breakfast meal is written into row address 1 at column address 1B, infusion dose data a2 for the breakfast meal is written into row address 2 at column address 1C and so on until the dose data a14 for the breakfast meal pattern is written into the row address E at column address 28. The insulin infusion doses a0 through a14 for the breakfast pattern are written into the memory across the data map in similar fashion up to the portion from row address 0 at column address 2A to row address E at column address 3D. Likewise, the insulin infusion doses b0 through b14 for the lunch pattern are written into the memory from row address 0 at column address 2B to row address E at column address 56. The insulin infusion doses c0 through c14 are written into the memory from row address 0 at column address 49 up to each of the row addresses at column address 5F and then, returning to column address 00, up to row address E at column address 27.

Since the infusion apparatus of the present invention is designed for use over an extended period of time, hypodermic injection is desirable to avoid phlebitis that often accompanies intravenous injection, bacterial infection from the point of insertion, and sclerosis of the blood vessel walls at the point of insertion. Since there is some time delay until the insulin can be absorbed into the blood through a hypodermic injection, it is necessary to take this time delay into consideration when deciding the infusion data for each meal pattern. An infusion data writing device, which will be described later, is employed to write the data into the memory map of the type shown in FIGS. 2A and 2B. The necessary data preferably is input to the writing device in advance, such data including not only the target insulin concentration in the blood, but also the patient's own insulin absorption rate, insulin excretion rate and distributed volume, and then written into the memory map at each of the addresses thereof. Thus the meal patterns are computed upon considering such data. For instance, though there are differences from patient to patient, blood sugar level will start rising about 15 minutes after the start of a meal, and a delay of about 45 minutes will be encountered before the insulin starts being absorbed into the blood through the hypodermic injection. Taking these factors into account, each meal pattern should increase the insulin dose from the normal level 30 minutes prior to the start of a meal, infuse an appropriately large dose of insulin just before and after the start of the meal, and then gradually reduce the insulin dose until the normal dose is attained almost four hours after the start of the meal pattern.

Accordingly, the storage of the meal patterns in the memory map of FIGS. 2A and 2B is accomplished by storing the supper pattern infusion dose c0 in the column addresses 00 through 19 at row address 0, the breakfast pattern infusion dose a0 in the column addresses 1A through 2F at the row address 0, the lunch pattern infusion dose b0 in the column addresses 30 through 48 of the row address 0, and the supper pattern infusion dose c0 in the column addresses 49 through 5F at the row address 0, by storing the supper pattern dose c1 in the column addresses 00 through 1A at the row address 1, the breakfast pattern dose a1 in the column addresses 1B through 30 at the row address 1, the lunch pattern infusion dose b1 in the column addresses 31 through 49 at the row address 1, and the supper pattern infusion dose c1 in the column addresses 4A through 5F at the row address 1. All the remaining meal pattern doses are stored in this fashion up to the row address E. Row address F, it will be remembered, stores the basic pattern, i.e., d0, d1, . . . and so on.

OPERATION OF THE INVENTION

Returning to FIGS. 1B and 1C, oscillator 10 constantly generates a high-frequency clock signal which is divided down by frequency dividers 14 and 18 to produce the one-minute pulses that are counted by counter 22. The outputs from counter 22 on lines 24A through 24G provide a seven-bit column address for the memory 26, as mentioned above. This represents time information which is incremented every 15 minutes, as described earlier. A meal switch 53 is depressed (closed) by the patient when a meal is to be consumed. When switch S3 is open, as illustrated in FIG. 1B, the output of AND gate 80 is low so that counter 34 cannot receive a reset signal. Under normal conditions, i.e., between meal patterns, the clock input to counter 34 is gated closed via AND gate 33 by the inverted high-level output of decoder 42, so that the counter 34 is held at the full count, as set forth above. The four outputs from counter 34 on lines 38A through 38D therefore are all high, so that row decoder 40 designates the row address F of memory 26. When the frequency divider circuit 18 delivers the one-minute clock pulse on line 21, the read/write circuit 44 responds by reading out the data which is stored at the point of intersection designated by the row address F and the column address that corresponds to the time information represented by the seven-bit data on lines 24A through 24G, obtained from counter 22. Thus, assuming that the time information is indicative of 05:00 (24-hour clock), read-write circuit 44 will read out the data d14 at the intersection of row address F and column address 14. The parity bit of the eight-bit data d14 is sent to the parity check circuit 70 through line 46H, while the remaining seven bits are sent to the presettable counter 48 as well as to the parity check circuit 70, through lines 46A through 46G. Owing to the one-minute clock pulse which it receives on line 21, the presettable counter 48 accepts the input seven-bit data as an initial or preset value. As a result, the output of counter 48 delivered on line 52 goes high, driving the motor M into rotation through the motor control driver circuit 54. As the motor M rotates, the preset value in the presettable counter 48 is decremented by the pulses generated by photosensor 68. The motor M continues rotating until the content of counter 48 is counted down to zero. When this occurs, the prescribed insulin dose will have been infused into the living body, upon which motor M is brought to rest instantaneously. Presettable counter 48, its content at zero, awaits the next one-minute clock pulse which will arrive on line 21. Thus, from 05:00 to 05:15, insulin is infused into the living body every minute at a dose corresponding to the infusion data d14. In other words, infusion is conducted in accordance with the basic pattern for the 15 minutes during which d14 is designated.

When the patient wishes to partake of a meal, he or she depresses the meal switch S3 30 minutes prior to the planned start of the meal. The four outputs 38A through 38D of counter 34 ordinarily are high, so that the output of decoder 42 on line 96 also is high, as mentioned above. Accordingly, closing the meal switch S3 sends the output of AND gate 80 high, whereby counter 34 is reset to zero, its four outputs 38A through 38D going low. When any one of these four outputs is low, the output of decoder 42 on line 96 will also be low, preventing the counter 34 from being reset, even if switch S3 is closed. When the four signals on lines 38A through 38D are not all high, this is sensed by the decoder 42 which responds by actuating a driver 86. The driver 86 in turn activates a light-emitting diode D3, presenting a visual indication which informs the patient of the fact that the meal pattern has been called.

Meanwhile, the row decoder 40 decodes the four signals received from counter 34 on lines 38A through 38D and designates the row address 0. Read/write circuit 44, responsive to the one-minute pulse which arrives on line 21, reads out the data stored at the point of intersection between the row address 0 and the column address that corresponds to the time information indicated by the signals from counter 22, delivered on lines 24A through 24G. For example, if the time is 07:00, read/write circuit 44 will read out the data a0 at the intersection of row address 0 and column address 1C. In other words, read/write circuit 44 reads out the initial insulin infusion dose d0 of the breakfast pattern. The seven bits (excluding the parity bit) that make up data d0 are applied to the presettable counter 48 and are preset in the counter in response to the one-minute clock pulse received on line 21. Thenceforth the counter 48 and motor control driver circuit 54 operate in the same fashion as described in connection with the basic pattern, whereby the motor M is rotated and the insulin infused for the period of time corresponding to the infusion data a0 preset in counter 48. The infusion operation for the breakfast pattern starts at time $t_1$ in FIG. 3A. Thus the breakfast pattern, shown in FIG. 3B, is called in place of the basic pattern. The breakfast pattern infusion data a0 is read out of the memory every minute until counter 34 counts 15 of the one-minute clock pulses arriving on line 36 to increment the row address indicated by the four bits on lines 38A through 38D. Motor M is therefore driven into rotation every minute to infuse the insulin dose corresponding to the infusion data a0. This action is repeated 15 times. Meanwhile, counter 22 also is counting the one-minute clock pulses on line 21. When the content of counter 22 is incremented after counting 15 of the one-minute clock pulses, the seven-bit time information delivered by the counter also is incremented, whereby the current column address of memory 26, such as column address 1C, is incremented to address 1D. If the row address designated by counter 34 at this time is still row address 0, however, then the insulin infusion data is still a0 and there is no change in the infusion dose. When counter 34 is incremented upon counting 15 of the one-minute pulses that arrive at its clock input, however, the row address designated by the four-bit counter output on lines 38A through 38D is incremented from 0 to 1, whereby the read/write circuit 44 reads out the dose data a1. This item of data is preset in presettable counter 48, so that motor M drives the feed pump 60 for a period of time corresponding to data a1, thereby infusing the prescribed insulin dose.

Counter 34 is successively incremented in the above fashion until its content attains the full count, which occurs 3 hours and 45 minutes after depressing meal switch S3. Thus, by way of example, if the meal switch S3 is depressed at exactly 07:00, counter 34 will attain the full count at 10:46, at which time its four outputs on lines 38A through 38D all go high. Decoder 42 senses this condition, thereby de-energizing driver 86 to deactivate the light-emitting diode D3. This indicates the end of the meal pattern. Since lines 38A through 38D are all high, row decoder 40 designates row address F so that the data read out of memory 26 is the data indicative of the basic pattern. In other words, assume that the column decoder 28 designates column address 2B at time 10:46, which is 3 hours and 45 minutes after the actuation of meal switch S3. Since row decoder 40 will designate row address F at this time, the basic pattern infusion data read out of the memory will be that which corresponds to the actual time, i.e., 10:46. Thus, upon the completion of the meal pattern, which is the breakfast pattern in this case, the basic pattern infusion data which prevails at that time will be restored.

Assume now that the patient, upon depressing the meal switch S3 to begin the infusion of a comparatively large dose of insulin, does not have his meal for some reason. This would place the patient in extreme danger since his blood sugar level will drop below the required minimum. To preclude this situation, the apparatus of the present invention is designed to inform the patient of the time at which the meal is to start, and to make it possible for him to change over the insulin infusion pattern from the meal pattern to the basic pattern immediately when the meal cannot be taken at the designated time for some reason.

To achieve the foregoing, the decoder 42 is adapted to deliver a high-level pulse on line 88 upon sensing that the four-bit binary number input from lines 38A through 38D has attained the value "2" (in decimal notation), which occurs when counter 34 has counted 30 of the one-minute clock pulses on line 36. The high-level signal on line 88 actuates a driver 90 to activate a light-emitting diode D4, thereby informing the patient of the fact that a meal is to start. The high-level signal on line 88 also enters the alarm circuit 74 which responds by producing an audible tone through energization of a sound-producing device BZ comprising a piezo-electric element or the like. The device BZ may be a buzzer or the like. The alarm circuit 74 receives also the signals of 2048, 4 and 2 Hertz supplied by the frequency divider 14 over line 16, and is adapted to actuate the buzzer BZ in response to these signals. The audible and visual information produced in the above manner inform the patient of the fact that a meal is scheduled to start.

When the patient is not capable of having the scheduled meal even though the meal time has arrived, he or she merely depresses switch S4. This causes AND gate 94 to deliver the high-frequency clock from frequency divider 14 to counter 34 through OR gate 32, AND gate 33 and line 36. As a result, the counter 34 is incremented up to the full count at an extremely rapid rate. Decoder 42 senses the full count and extinguishes light-emitting diode D3 via driver 86. At the same time, the output of decoder 42 on line 96 goes high and is inverted by inverter 30, thereby closing AND gate 33 so that counter 34 is no longer capable of counting the clock pulses. In other words, the clock input is disabled when counter 34 reaches the full count. Thereafter, counter 34 holds the full count so that row decoder 40 designates the row address F of memory 26 continuously. The read/write circuit 44 consequently reads out the basic pattern infusion data stored at the intersection between row address F and the column address corresponding to the time at which the cancel switch S4 was depressed. From that time onward the insulin is infused in accordance with the basic pattern.

Figure 3E:
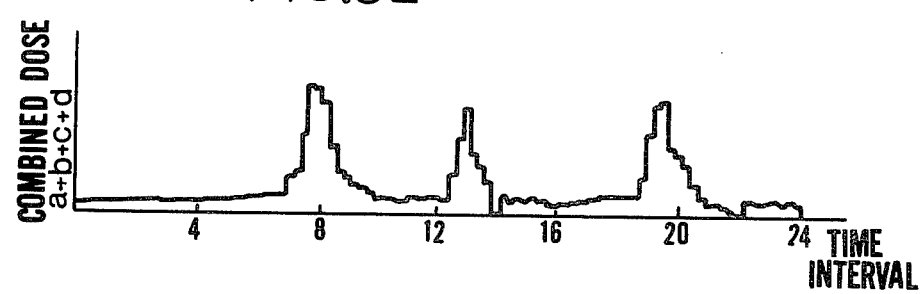

In accordance with the present invention as described above, the meal patterns which are available are the breakfast, lunch and supper patterns. The selection of the particular pattern will depend upon the time at which the meal switch S3 is depressed. Referring now to row address 0 at which the initial items of infusion data for each of the meal patterns are stored, it will be seen that the initial item of infusion data c0 for the supper pattern is stored at column addresses 00 through 19, that the initial item of infusion data a0 for the breakfast pattern is stored at column addresses 1A through 2A, that the initial item of infusion data b0 for the lunch pattern is stored at column addresses 2B through 48, and that the initial item of infusion data c0 for the supper pattern is stored at column addresses 49 through 5F. Accordingly, depressing the meal switch S3 between 06:30 and 11:59 calls the breakfast pattern a, depressing it between 12:00 (noon) and 18:14 calls the lunch pattern b, and depressing it between 18:15 and 06:29 of the following day calls the supper meal pattern c. FIGS. 3A, 3B, 3C, 3D and 3E show an example wherein the meal switch S3 is depressed at times $t_1$, $t_2$, $t_3$, as illustrated in FIG. 3A, in order to call the breakfast, lunch and supper meal patterns, respectively, as depicted in FIGS. 3B, 3C and 3D. FIG. 3E illustrates the combined insulin infusion pattern over a period of 24 hours for a case where the three meal patterns are called at the three specified times $t_1$, $t_2$, $t_3$.

The infusion apparatus must have a high degree of reliability since the hypodermically inserted needle 64 is required to dispense the prescribed insulin dose once per minute while the apparatus itself is carried by the patient. To achieve such reliability, the apparatus power system is designed to provide a redundancy feature, which will now be described.

The power system includes a main power supply 100 and back-up or auxiliary power supply 102, as shown in FIG. 1C. These are rechargeable batteries which enable replacement of the main power supply battery without loss of power to the critical circuit components. Specifically, the main power supply 100 provides power to the light-emitting diodes D3 through D7, buzzer BZ and motor M, etc. The auxiliary power supply 102 supplies the power for the oscillator 10 and other circuitry including memory 26 at all times, and is charged in small increments by main power supply 100 under ordinary conditions. Accordingly, though the battery of main power supply 100 is, preferably, exchanged once a day for the purpose of charging, auxiliary power supply 102 continues to supply power during the exchange operation to preserve the data stored in memory 26 and to assure that the clock circuitry inclusive of the oscillator 10 will continue functioning.

Althgough this will be discussed in further detail later, a medication bag 200 (FIG. 4), filled with insulin or other liquid medication, is connected to the feed pump 60. The medication bag 200 also should be replaced for the purpose of refilling once a day, this being carried out advantageously at the same time that the battery of the main power supply is replaced for recharging. The time at which the exchange is to be effected can be indicated by means of a light-emitting diode D5 and the buzzer BZ. This may be accomplished by programming the exchange time into the memory map of FIG. 2, as by reversing the ordinary parity of the data items at each of the row addresses that intersect the column address corresponding to the time at which the exchange is to be performed. By way of example, assume that the parity check circuit 70 in this embodiment of the apparatus is adapted to check for odd parity. Then, if the exchange is to take place at, say, 10:00, even parity bits would be assigned to all the items of infusion data at row addresses 0 through F where they intersect the column address 28, since this is the address corresponding to 10:00. Whenever read/write circuit 44 reads an item of data out of the column address 28, therefore, parity check circuit 70 issues a high-level output on line 72 since the sensed parity is not odd. The high-level signal, which is coupled to the alarm circuit 74, causes the alarm circuit to activate buzzer BZ and light-emitting diode D5, thereby informing the patient that the time has arrived to exchange the battery of main power supply 100 as well as the medication bag 200. Another safety feature of the apparatus is light-emitting diode D6. When the main power supply 100 or auxiliary power supply 102 experiences a drop in voltage, this is sensed by the alarm circuit 74 which responds by activating the light-emitting diode D6 to provide a visual indication of the fact. The alarm circuit 74 is adapted to activate the buzzer BZ as well.

Another possible source of trouble that can lead to abnormal infusion is the medication feed system, which includes the feed pump 60, photosensor 68 and the like. The alarm circuit 74 is adapted to activate the light-emitting diode D7 and buzzer BZ in the event of a feed system failure. To this end, the alarm circuit 74 includes a timer (not shown) for monitoring the peiord of time between the actuation and halting of motor M by means of the motor control driver circuit 54. The timer is set to a time value which is greater than the maximum value of any item of infusion data stored in the memory map of FIGS. 2A and B. In other words, the set time is somewhat longer than that required to infuse the maximum insulin dose with a single infusion operation. Thus, if a problem should develop in the feed system and cause motor M to continue rotating for a period of time in excess of the set time, this is sensed by the timer in the alarm circuit 54 which responds by forcibly deenergizing the motor control driver circuit 54 in order to stop the motor M, and by activating the buzzer BZ and light-emitting diode D7 to warn the patient. This feature of the apparatus prevents the infusion of an insulin overdose. It should be noted that switch S2 is a switch for resetting the alarm.

Figure 5:
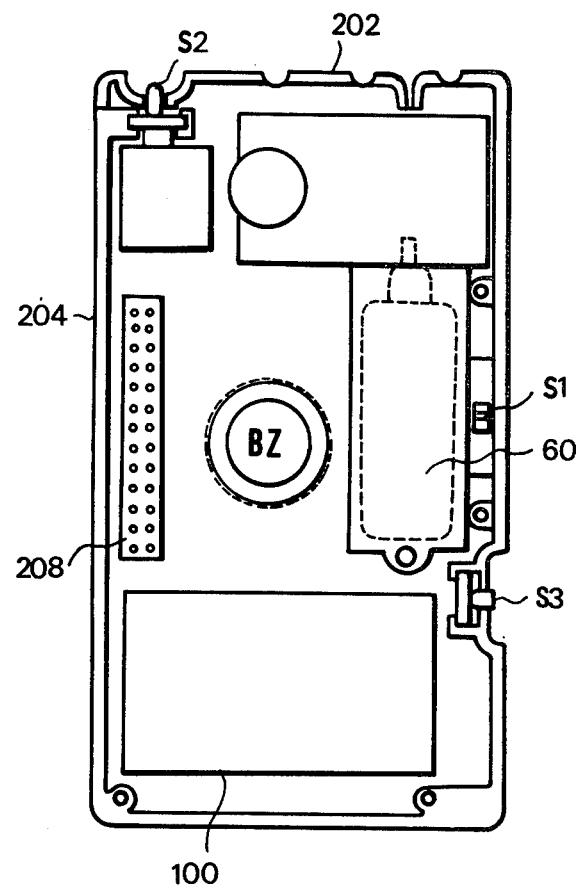
FIG. 5 is a plan view of the apparatus with the cover removed.
Figure 6:
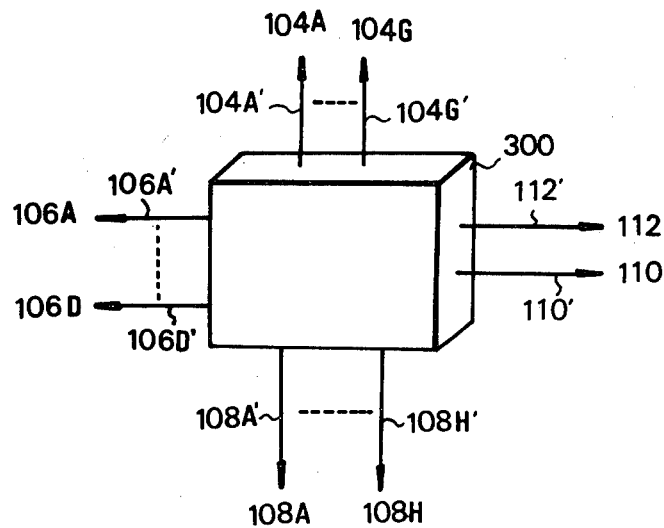
FIG. 6 is a block diagram showing the connection relationship between the leads on an externally located infusion data writing device, and the leads to the medication infusing apparatus.

A characterizing feature of the invention infusion apparatus is that an office computer such as a microcomputer or minicomputer can be used to write the infusion data into the memory map of memory 26. To this end, as shown in FIG. 5, various leads connected to the memory 26 can be led out by being connected to an external connector 208 having a number of terminals. These terminals are connected to column address designating leads 104A through 104G, row address designating leads 106A through 106D, data writing leads 108A through 108H, a write enable lead 110 and a clock input terminal 112, etc. In addition, the power supply terminals of memory 26 also are led out as external connection terminals, but these are not shown. When writing data into the memory 26, the connections are as shown in FIG. 6. Specifically, the column address designating leads 104A through 104G are connected to the corresponding column address designating leads 104A' through 104G' of an externally provided infusion data writing device 300, such as the office computer mentioned above. Further, the row address designating leads 106A through 106D are connected to the corresponding row address designating leads 106A' through 106D' of the device 300, the data writing leads 108A through 108H are connected to the corresponding data output leads 108A' through 108H' of device 300, and the write enable lead 110 is connected to the write lead 110' of the device 300. (Since the memory is asynchronous, a special clock is not employed.)

When the infusion data writing device 300 is connected to the infusion apparatus of this invention, therefore, the circuitry for driving the column decoder 28 and row decoder 40 will in effect connect with the circuitry of the apparatus and the circuitry of the writing device 300. However, if the resistance values of the resistors R1A through R1G, R3A through R3D and R6 that are connected to each of the abovementioned leads are selected to be sufficiently large with respect to the impedence of the infusion data writing device 300, then the writing device 300 will be able to designate the addresses of the column decoder 28 and row decoder 40 without influencing the output signals from counters 22 and 34. With this arrangement, then, the infusion data writing device 300 designates the row and column addresses of memory 26 and writes in the data from data input terminals 108A through 108H.

Figure 7:
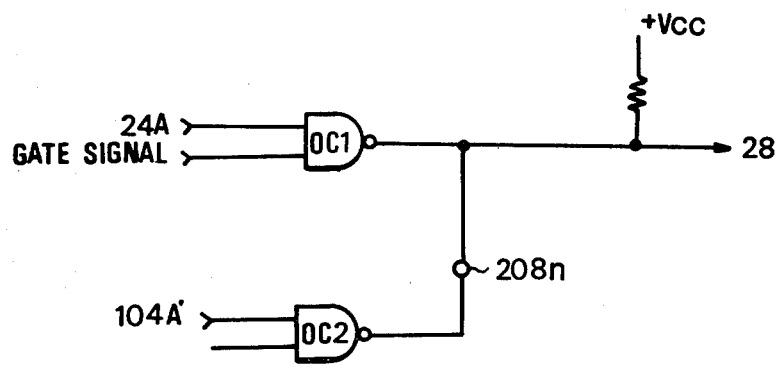
FIG. 7 is a sketch of an impedance control circuit for regulating the impedance on the infusing apparatus side when the apparatus is connected to the infusion data writing device.
Figure 8:
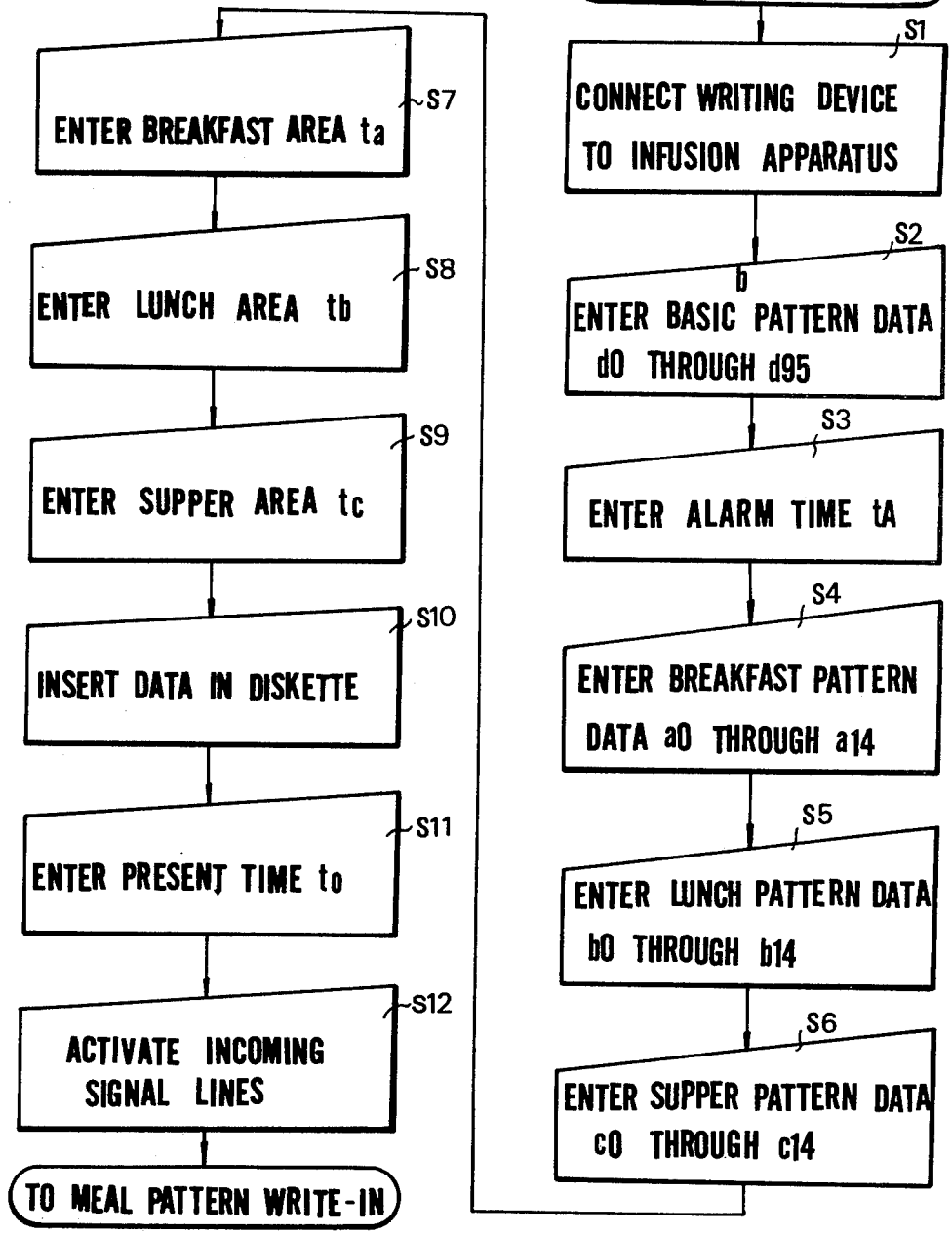
FIG. 8 is a flowchart showing preparatory steps for writing in data.

A circuit arrangement of the type shown in FIG. 7 can be adopted for each of the resistors R1A through R1G, R3A through R3D and resistor R6, the impedences of which are to be set high when the infusion data writing device 300 is connected to the infusion apparatus. Taking resistor R1A as an example, a wired OR circuit may be constructed from a NAND gate OC1 of open collector type having one input connected to the output line 24A of counter 22 while the other input receives a gating signal, and a NAND gate OC2, also of open collector type, having one input terminal for receiving the address (clock) from the infusion data writing device 300. The gate input terminal to NAND gate OC2 is open. The gating signal applied to NAND gate OC1 is set low (logic "0") when data is to be written in from the writing device 300, and set high (logic "1") when the infusion apparatus is operating in the ordinary manner described hereinabove. FIG. 7 also shows one of the connector pins 208N in the external connector 208, shown in FIG. 5.

After the infusion data writing operation is completed, the clock input terminal 112 of the infusion apparatus is connected to the clock output terminal 112' of the infusion data writing device 300 to receive a time adjustment clock for the purpose of setting the time in counters 22, 34 to the standard time. In another preferred embodiment, an EPROM may be used as the memory 26. Such an expedient allows the auxiliary power supply to be dispensed with since the program (the infusion data), once written, will not be erased even if power is cut off. It also eliminates the need for a connector for connecting the infusion apparatus to the writing or programming device. Instead, the EPROM can be replaced through use of an IC socket. Accordingly, an EPROM programmed by the programming device need only be plugged into the IC socket. If a number of EPROMs are prepared and preprogrammed to include a variety of infusion data, the programmed infusion patterns can be changed merely by unplugging one EPROM and exchanging it for another, without requiring that the programming or writing device be connected to the infusion apparatus each time to rewrite the data in the memory. A system of this type is very convenient for a physician making a house call since he need not carry the programming device, which ordinarily is large in size.

The programming or infusion data writing device may conveniently employ a personal computer of the type which relies upon a floppy disk. In the embodiment of the present invention, a floppy disk is prepared for storing various programs such as the OS (operating system) of the system, as well as a data file floppy disc capable of storing the insulin infusion data for 500 patients.

A program disk stores programs which determine the optimum infusion pattern and infusion parameters based on the analytical data for the particular patient, an infusion data input program for entering infusion data, which enters from a keyboard, into the data file disk, as well as a data transfer program for transferring the infusion data of the data file to the memory 26 of the medication infusing apparatus.

The infusion data is entered from a keyboard under the control of the infusion data input program in the following order, which serves merely as an example: the basic pattern infusion dose (96 items of data), the breakfast, lunch and dinner pattern infusion doses (15 items of data each), the meal pattern changeover times (three items of data), and the alarm time (one item of data) for the replacement of the battery and/or medication bag.

The transfer of infusion data to the medication infusing apparatus takes place under the control of the data transfer program. The patient's infusion data stored in the data file disk, following temporary storage in the memory device of a computer, is transferred for storage, in the form of eight parallel bits, to the memory 26 of the medication infusing device through the computer interface. For example, this may be accomplished by storing the data starting from row address 0 and column address 00 and proceeding until row address 0 and column address 5F, then from row address 1 and column address 00 until row address 1 and column address 5F, and so on until row address F and column address 5F.

The patient's insulin infusion data is thus stored in memory 26 in the form of the memory map shown in FIGS. 2A and 2B. After the infusion data is written, the writing device is disconnected from the external connector 208, with no danger of erasing the content of memory 26. Furthermore, the patient cannot rewrite the data in memory 26 of his own accord if he does not have access to the writing device, which is located at a hospital or clinic and is operated exclusively by the physician. The medication infusing apparatus, on the other hand, is portable and is carried by the patient, who is taught how to exchange the medication bag and battery and how to charge the battery.

Referring now to the flowchart of FIGS. 8 through 12, a detailed discussion will be had regarding the writing of a program by means of the infusion data writing device 300.

The first step S1 is to connect the infusion data writing device to the medication infusing apparatus of the invention. Step S2 is to enter the basic pattern data d0 through d95. Step S3 is to enter an address tA corresponding to the time 16:30 at which the medication bag 200 is to be replaced, as well as the battery of main power supply 100 for the purpose of recharging. In step S4, the breakfast pattern data items a0 through a14 are entered. The lunch pattern data items b0 through b14 are entered in step S5, and the supper pattern data items c0 through c14 in step S6. The breakfast meal area ta is entered in step S7. The breakfast meal area ta refers to the starting address of the memory at which the breakfast pattern is to be written. The lunch and supper areas tb, tc are entered in steps S8 and S9, respectively. The areas tb, tc are the starting addresses of the lunch and supper meals, respectively.

Next, the data is stored in a diskette in step 10, and the present time t₀ is entered in step S11. This is for the purpose of setting the infusion data writing device 300 to the present time prepraratory to setting the present time in the infusion apparatus, which will take place later.

Control next shifts to step S12, in which the signal lines from the writing device 300 are activated. In other words, the gating signal applied to NAND gate OC1 in FIG. 7 is set to the low level through an interface, not shown.

The execution of the foregoing steps completes the preparation of the written data as well as the connection between the writing device 300 and the medication infusing apparatus of the invention. The writing of the meal patterns into the infusion apparatus is now ready to begin, as will be described with reference to FIG. 9.

In step S13, row address RA is set to "0", and in step S14, the starting address ta of the breakfast pattern is set to column address CA. In step S15, $\alpha$ is set to RA, that is, to "0". Breakfast pattern data a$\alpha$ (a0) is written into the designated address MA of the memory in step S16. In step S17 the column address is updated by "1", and in step S18 it is discriminated whether CA=tb. When the writing of the breakfast pattern area is incomplete (CA≠tb), that is, when the result of the discrimination operation is "No", control returns to step S16 to effect the writing of data into the updated memory address. The above writing operation is repeated until it is discriminated that CA=tb, during which time a$\alpha$, namely the breakfast pattern data a0, is written into column addresses 1A through 2F at row address 0. The writing of this item of data ends when CA=tb is found th hold in step S18; control then shifts to step S19 for the writing of the lunch pattern. In this step, b$\alpha$, namely the lunch pattern data b0, is written into the designated address MA of the memory. Step S20 serves to increment the column address CA by "1" to update the address, and step S21 serves to discriminate whether CA=tc. When the result is "No", control returns to step S19 where the lunch pattern data b0 is written into the updated memory address. The writing of this item of data ends when the result of discriminating CA=tc is "Yes" in step S21, this occurring when the writing operation has been executed up to column address 48. Thenceforth control shifts to step S22, which serves to write the supper pattern data c$\alpha$, namely c0, into the designated address MA of the memory. In step S23, column address CA is updated by "1". In step S24, it is discriminated whether CA=ta. When the result is "No", control returns to step S22 until the supper pattern data c0 is written up to column address 19. The completion of this writing operation is sensed in step S24, with control then shifting to step S25. Here the breakfast, lunch and supper pattern areas ta, tb, tc and row address RA are each updated by "1". Step S26 serves to discriminate whether RA=15. When the result is "No", control returns to step S14 where the updated meal patterns are written into the corresponding writing areas of the updated respective row addresses. This is executed until RA=15 is detected, at which time the writing of the meal patterns ends and control shifts to the writing of the basic pattern, as shown in FIG. 10.

Figure 10:
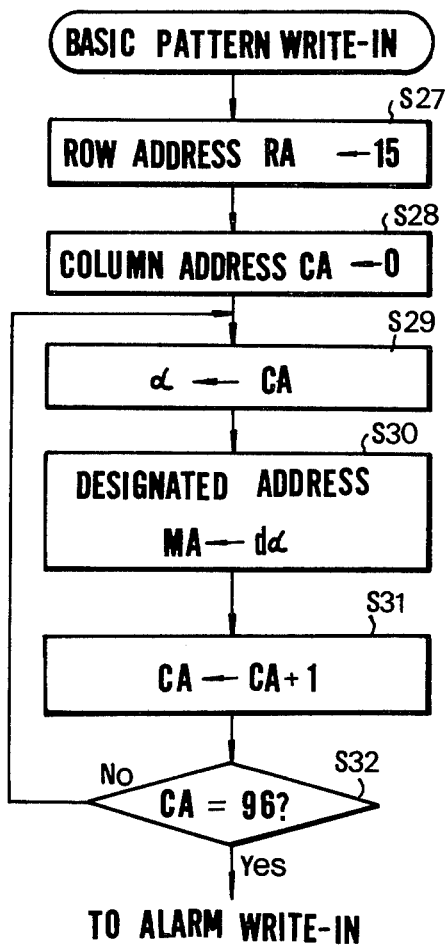
FIG. 10 is a flowchart showing steps for writing in basic pattern data.
Figure 12:
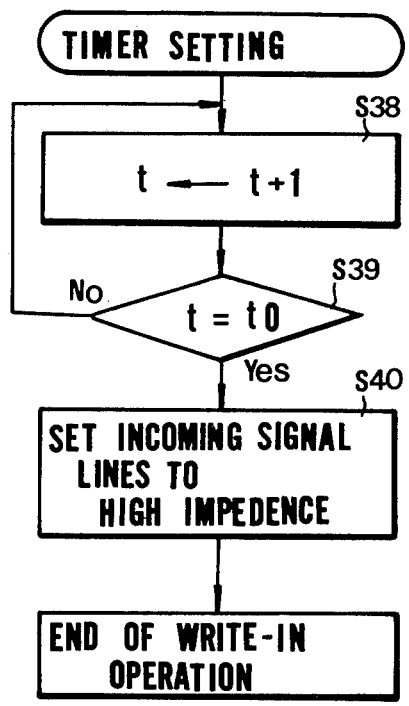
FIG. 12 is a flowchart showing steps for setting a timer.

Step S27 in FIG. 10 serves to set the row address RA to "15", and step S28 serves to set the column address CA to "0". In step S29 $\alpha$ is set to "0", and in step S30 the basic pattern data d$\alpha$ is written into the memory address MA designated by the column and row addresses. Step S31 serves to update the column address CA by "1" to write the basic pattern d$\alpha$. This is executed up to column address 5F (95). When CA=96 is found to hold in step S32, control shifts to the writing of the alarm data, as shown in FIG. 11.

Figure 11:
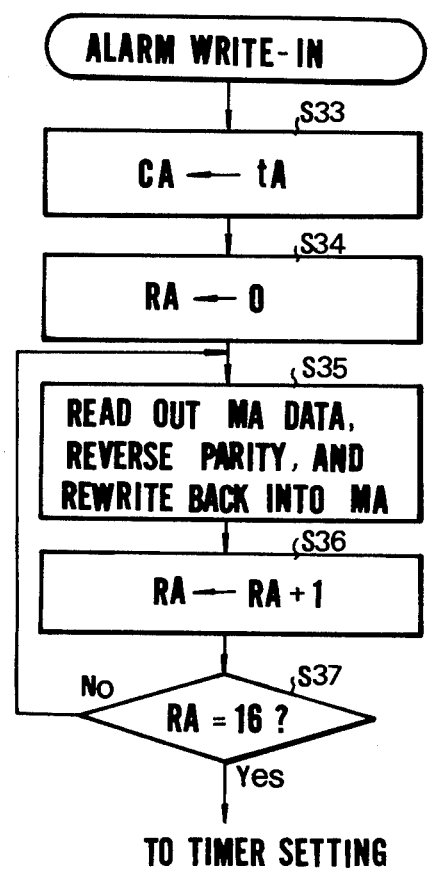
FIG. 11 is a flowchart showing steps for writing in alarm data.

Step S33 in FIG. 11 serves to set the column address CA to the column address tA which corresponds to the alarm time for replacement of the battery and/or medication bag, and step S34 serves to set the row address RA to "0". In step S35, the data is read out of the address MA specified by column address CA and row address 0, the parity of the data is reversed, and the data is then written back into said address. Next, step S36 serves to update row address RA by "1", and step S37 discriminates whether or not RA=16. When the result of the discrimination is "No", step S35 is restored to reverse the parity of the item of data at the next specified address. This is repeated until RA=16 is detected in step S37, at which time control shifts to the timer setting of step S38, illustrated in FIG. 12. In step S38, "1" is added to the time t of the timer, with the sum being designated t. In step S39, the present time t₀ and time t are compared; when t=t₀, the time adjustment of the medication infusing apparatus ends. Control then shifts to step s40, in which the incoming signal lines are set to a high impedance. At the same time, the gating signal applied to the NAND gate OC1 is set to the high level. This completes the operations for writing in the various patterns and for the time adjustment.

Figure 4:
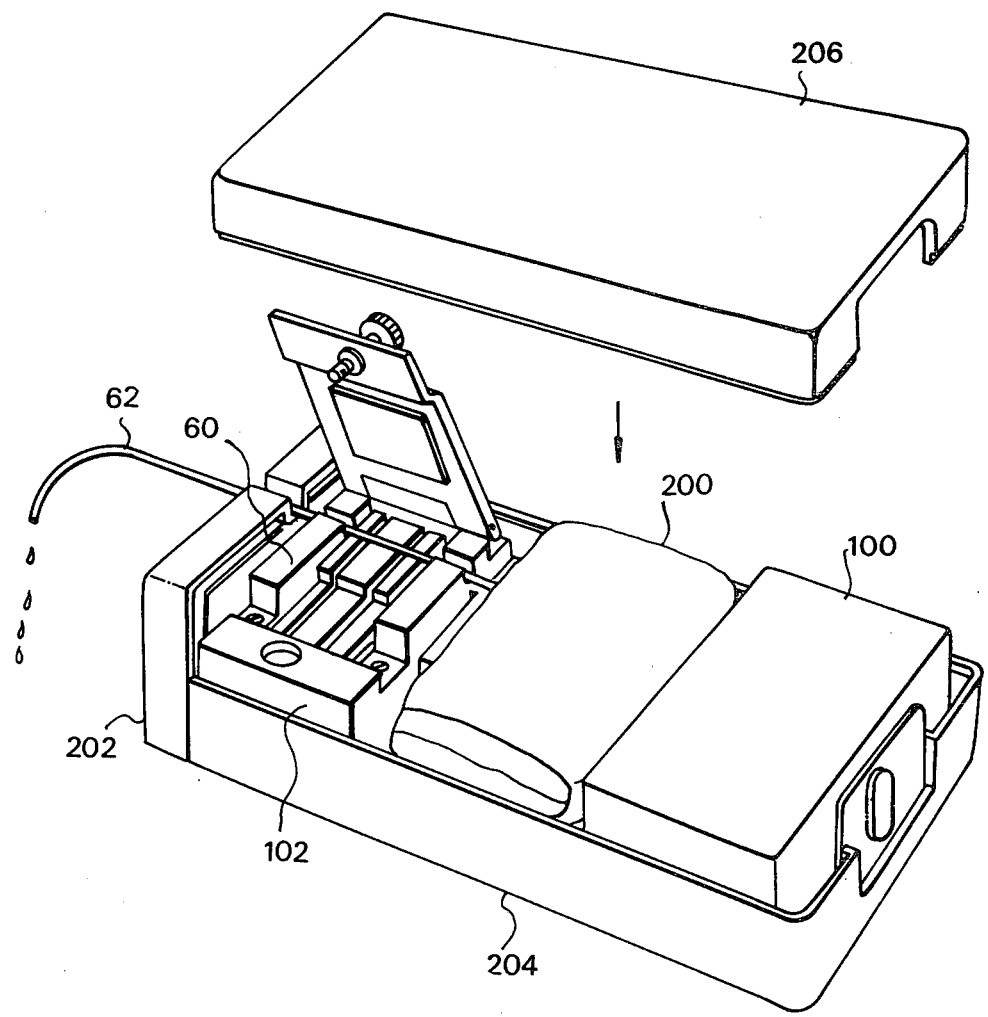
FIG. 4 is a perspective view showing the external appearance of a medication infusion apparatus according to the present invention.

The external configuration of the medication infusing apparatus is depicted in FIG. 4. The entire apparatus is mounted on a holder so as to fit under the patient's left arm. The medication feed tube 62 is led out from the upper part of the apparatus and the area around its dispensing port is smoothly shaped to preclude blockage even when the tube is bent. The light-emitting diodes and the switches are mounted on a control panel 202. A case 204 having a cover 206 accommodates the batteries 100, 102 serving as the main and auxiliary power supplies, respectively, the medication bag 200, as well as the feed pump 60 which may comprise a peristaltic finger pump having, e.g. three fingers. The other components such as the motor M, buzzer BZ and connector 208 for the connection to the infusion data writing device 300 are attached to the case but not illustrated in the Figure.

EFFECTS OF THE INVENTION

The programmable medication infusing apparatus of the present invention, having the construction described and illustrated hereinabove, exhibits the following effects. First, the basic pattern for the infusion of medication can be finely set at 15-minute intervals in accordance with the patient's condition. Next, the meal patterns can be set, also at 15-minute intervals, independently of the basic pattern and independently of one another. Since the basic pattern and meal patterns are synchronized along a time axis, the changeover between the basic pattern and a meal pattern is accomplished by an interrupt action based on time. Thus, a meal pattern can be selected in accordance with the time at which the interrupt is generated. When returning from a meal pattern to the basic pattern, moreover, the basic pattern that is restored corresponds to the time at which the return is effected.

These fundamental effects of the invention make it possible to achieve long-term control of the blood sugar level best suited for the particular needs of a diabetic patient. For example, since the insulin infusion pattern required for a meal will not be established unless the patient depresses the meal switch, even socially active patients who tend to have their meals irregularly can regulate their blood sugar to a level commensurate with such circumstance. Such an individual therefore has the option of eating whenever he or she so desires.

The present invention is advantageous also in that the basic pattern and meal pattern doses can be changed to take into account such factors as the patient's condition, age, sex and activity. Furthermore, if the patient depresses the meal switch inadvertently or does not actually have a meal after depressing the switch, the infusion apparatus of the invention is adapted to issue an alarm a predetermined length of time after closure of the switch in order to gain the attention of the patient. The patient is therefore given the opportunity to depress the meal cancel switch in order to effect the change from the meal pattern to the basic pattern, the infusion dose whereof will depend upon the actual time. This eliminates the danger of a low blood sugar level arising from an insulin overdose. In addition, since the infusion data writing device is constructed as a unit separate from the infusion apparatus, the patient cannot rewrite the data in the memory of the apparatus either accidentally or intentionally.

The medication infusing apparatus of the present invention has been described and illustrated in connection with an embodiment wherein the apparatus is employed to infuse insulin into a living body, but the invention is in no way limited to such use. For example, in the illustrated embodiment, use is made of a memory map in which the column addresses correspond to actual time and the row addresses correspond to the temporal change of the basic pattern and meal patterns. However, it is not necessary to adopt such a matrix array, for it is obvious that a memory configuration can be employed wherein the particular meal pattern called will correspond to the length of time the meal switch is held depressed. In addition, though the memory is realized through CMOS technology, an alternative approach is to realize the memory and peripheral circuitry by means of a microcomputer. And, though the illustrated embodiment employs CMOS technology and a hybrid integrated circuit, it is obvious that a bipolar integrated circuit may be used.

The infusion doses of the basic pattern are spread out over a 24-hour period in the illustrated embodiment. Depending upon the patient's condition, however, it is possible to adopt a different distribution. Moreover, while each meal pattern is spread over a period of 3 hours and 45 minutes, meal patterns of a different duration can be programmd into the apparatus with facility. Although the infusion of medication is effected once per minute and the infusion dose is variable at 15-minute intervals in the illustrated embodiment, these figures are not restrictive in nature. It should also be noted that the meal patterns need not be of equal duration.

As many apparently widely different embodiments of the present invention may be made without departing from the spirit and scope thereof, it is to be understood that the invention is not limited to the specific embodiments thereof except as defined in the appended claims.

What is claimed is:
1. An apparatus for infusing liquid medication, comprising:
   time base means for generating time information;
   memory means for storing first infusion information indicative of a liquid medication infusion dose which varies with time information generated by said time base means, and second infusion information corresponding to a meal pattern determined by the time information generated by said time base means;
   first addressing means for effecting an address designation in accordance with said time information upon establishing correspondence between a portion of address information for reading out information stored in said memory means, and said time information;
   second addressing means for designating respective addresses in accordance with which of the first and second infusion information is selected, a first specific address being designated when said first infusion information is selected, a second specific address being designated when said second infusion information is selected, said second specific address being updated in accordance with time until the designated address returns to said first specific address of said first infusion information; and
   infusion means driven in accordance with infusion information read out of said memory means for infusing said liquid medication into a living body.
2. The apparatus according to claim 1, in which said memory means includes a plurality of storage locations at the points of intersection between a set of row addresses and a set of column addresses, one set being decided in accordance with the time information, the other set being allocated in accordance with the first and second infusion information.
3. The apparatus according to claim 1, in which said infusion means is constructed and arranged to infuse insulin into the living body, the first infusion information is a basic pattern, and the second infusion information is a meal pattern different from said basic pattern and including at least one pattern selected from among a breakfast pattern, lunch pattern and supper pattern.
4. The apparatus according to claim 1, in which said infusion means includes a motor driven at a substantially constant speed by a control signal for infusing the liquid medication into a living body, and including a memory control circuit means for reading infusion doses out of said memory means at fixed time intervals, said apparatus further including control signal generating means for generating said motor control signal for a period of time corresponding to the dose read out of said memory means by said memory control circuit means.
5. The apparatus according to claim 1, including a plurality of frequency divider stages, and in which said first addressing means and said second addressing means include first and second counters, respectively, for counting clock pulses from said time base means following division by said plurality of frequency divider stages.
6. The apparatus according to claim 5, further comprising a discrimination circuit for discriminating a first specific counted value in said second counter to produce an inhibit signal which inhibits said second counter from counting the clock pulses, whereby said second counter preserves said specific count as an address of said first infusion information.

7. The apparatus according to claim 6, including alarm means and in which said discrimination circuit means is adapted to discriminate a second specific counted value in said second counter for driving said alarm means when said second specific counted value is discriminated, whereby said alarm means informs the patient of the fact that a predetermined period of time has elapsed since the selection of said second infusion information.

8. The apparatus according to claim 6, further comprising reset means for resetting said second counter preserving said first specific counted value, whereby said second counter is preset to a specific value which corresponds to an address of said second infusion information.

9. The apparatus according to claim 8, in which the counted value in said second counter, which varies from said preset specific value to said first specific value, is continuously allocated to the addresses that designate said first and second infusion information.

10. The apparatus according to claim 4, in which said reset means comprises a second infusion information selection switch which is operative from outside the apparatus.

11. The apparatus according to claim 5, further comprising selection means for selectively supplying said second counter of said second addressing means with said frequency-divided clock pulses, and with second clock pulses n-times higher in frequency concurrently provided by an earlier stage of the plurality of frequency divider stages, wherein n is a positive integer.

12. The apparatus according to claim 11, in which said selection means comprises a switch for interrupting the read-out of said second infusion information.

13. An apparatus for infusing liquid medication, comprising:

time base means for generating time information;

readable/writable memory means for storing first infusion information indicative of a liquid medication infusion dose which varies with time information generated by said time base means, and second infusion information corresponding to a meal pattern determined by the time information generated by said time base means;

first addressing means for effecting an address designation in accordance with said time information upon establishing correspondence between an address of said memory means and said time information;

first selection means coupled to the output side of said first addressing means for selectively receiving address designating signals from said first addressing means and externally applied address designating signals;

second addressing means for designating an address in accordance with which of the first and second infusion information is selected, a first specific address being designated when said first infusion information is selected, a second specific address being designated when said second infusion information is selected, said second specific address being updated in accordance wih time until the designated address returns to said first specific address of said first infusion information;

second selection means coupled to the output side of said second addressing means for selectively receiving address designating signals from said second addressing means and externally applied address designating signals;

data input means for receiving externally written data;

means for controlling the writing and reading of data to and from said memory means;

write signal input means for applying a write control signal to said write/read control means when data is externally written;

means for generating an internal clock applied to said write/read control means;

high-impedance setting means connected to the output side of said internal clock generating means for selectively receiving said internal clock and an externally applied clock; and infusion means driven in accordance with infusion information read out of said memory means for infusing said liquid medication into a living body.

14. The apparatus according to claim 13, including input terminals for receiving externally applied address inputs, data inputs, a write control signal input and a clock input.

* * * * *